United States Patent
Pagani et al.

(10) Patent No.: US 9,119,895 B2
(45) Date of Patent: Sep. 1, 2015

(54) SELF-ADHESIVE MATRIX SYSTEM COMPRISING A STYRENE BLOCK COPOLYMER

(75) Inventors: Stefania Pagani, Sesto San Giovanni (IT); Maurizio Di Grigoli, Sesto San Giovanni (IT); Sergio Comuzio, Sesto San Giovanni (IT)

(73) Assignee: BOUTY S.P.A., Sesto San Giovanni (IT)

( * ) Notice: Subject to any disclaimer, the term of this patent is extended or adjusted under 35 U.S.C. 154(b) by 1084 days.

(21) Appl. No.: 13/133,687

(22) PCT Filed: Dec. 10, 2009

(86) PCT No.: PCT/EP2009/008826
§ 371 (c)(1),
(2), (4) Date: Jun. 21, 2011

(87) PCT Pub. No.: WO2010/066424
PCT Pub. Date: Jun. 17, 2010

(65) Prior Publication Data
US 2011/0243985 A1    Oct. 6, 2011

(30) Foreign Application Priority Data

Dec. 11, 2008 (IT) .............................. MI2008A2186

(51) Int. Cl.
| | |
|---|---|
| *A61L 15/44* | (2006.01) |
| *A61K 8/02* | (2006.01) |
| *A61K 8/37* | (2006.01) |
| *A61K 8/90* | (2006.01) |
| *A61K 8/92* | (2006.01) |
| *A61K 9/70* | (2006.01) |
| *A61L 15/58* | (2006.01) |
| *A61Q 19/00* | (2006.01) |
| *C08L 91/08* | (2006.01) |
| *C09J 123/08* | (2006.01) |
| *C09J 153/02* | (2006.01) |
| *C09J 125/08* | (2006.01) |
| *C09J 109/06* | (2006.01) |
| *C09J 123/22* | (2006.01) |
| *C08L 23/00* | (2006.01) |
| *C08L 53/02* | (2006.01) |

(52) U.S. Cl.
CPC ............... *A61L 15/44* (2013.01); *A61K 8/0208* (2013.01); *A61K 8/37* (2013.01); *A61K 8/90* (2013.01); *A61K 8/922* (2013.01); *A61K 9/7053* (2013.01); *A61L 15/585* (2013.01); *A61Q 19/00* (2013.01); *C08L 91/08* (2013.01); *C09J 123/08* (2013.01); *C09J 153/025* (2013.01); *A61K 9/7076* (2013.01); *A61K 2800/10* (2013.01); *A61L 2300/802* (2013.01); *C08L 23/00* (2013.01); *C08L 53/02* (2013.01); *C09J 109/06* (2013.01); *C09J 123/22* (2013.01); *C09J 125/08* (2013.01)

(58) Field of Classification Search
CPC ...... C09J 109/06; C09J 123/08; C09J 123/22; C09J 125/08
USPC .................................. 424/447; 524/502, 571
See application file for complete search history.

(56) References Cited

U.S. PATENT DOCUMENTS

| | | | |
|---|---|---|---|
| 4,728,572 A | 3/1988 | Davis | |
| 5,143,972 A * | 9/1992 | Groves | ........................... 525/71 |
| 5,527,536 A | 6/1996 | Merkle et al. | |

FOREIGN PATENT DOCUMENTS

| | | | |
|---|---|---|---|
| EP | 0885942 A | | 12/1998 |
| WO | WO-98/28015 | * | 7/1998 |
| WO | WO 99/53357 A | | 10/1999 |

\* cited by examiner

*Primary Examiner* — Ali Soroush
(74) *Attorney, Agent, or Firm* — Silvia Salvadori, P.C.

(57) ABSTRACT

Disclosed is a self-adhesive matrix system comprising a styrene-ethylene/butylene-styrene (SEBS) copolymer in an oil/ethyl acetate mixture, a hydrogenated resin and a pharmaceutical or cosmetic active ingredient.

10 Claims, No Drawings

SELF-ADHESIVE MATRIX SYSTEM COMPRISING A STYRENE BLOCK COPOLYMER

CROSS REFERENCE TO RELATED APPLICATIONS

The present application is a 35 U.S.C. §371 National Phase conversion of PCT/EP2009/008826, filed Dec. 10, 2009, which claims benefit of Italian Application No. MI2008A002186, filed Dec. 11, 2008, the disclosure of which is incorporated herein by reference. The PCT International Application was published in the English language.

The present invention relates to a self-adhesive matrix system comprising a styrene-ethylene/butylene-styrene (SEBS) copolymer solubilised in an oil/ethyl acetate mixture.

PRIOR ART

Patches are used as medical devices to protect skin wounds and sores, and in the pharmaceutical industry to deliver active ingredients or cosmetics.

In both cases, the simplest and most advantageous configuration in terms of industrial production is a flexible backing designed to protect and support the pharmaceutical form, an adhesive matrix (which may control the release of the active ingredient and allow close contact with the skin surface), and a protective sheet designed to be removed at the time of use.

The polymer matrices used in the development of medicated and transdermal patches mainly consist of "pressure-sensitive adhesives" (PSA), defined as adhesive materials that form a bond with the surface they come into contact after the application of slight pressure, and that can be removed without causing pain or leaving visible residues on the skin.

PSAs can be used in a wide range of applications as adhesive systems in patches for topical use, because they present excellent properties of adhesion, both at the time of application and for prolonged periods, are compatible with active ingredients, and govern their release through the skin surface.

PSAs can be classified on the basis of the physical form in which they are sold, or their chemical structure. Two main categories can be distinguished on the basis of physical form: in solution or dispersion (where the solvent can be aqueous or organic), and hot-melt adhesives.

At present, the most widely used PSAs are based on organic solvents, although the use of PSAs with an aqueous or hot-melt base has the advantage of reducing the risk of skin irritation and sensitisation and environmental contamination.

The crucial pre-requisite for correct adherence to a soft tissue like the skin is that the polymer possesses good viscoelastic properties. Among the available adhesives, hot-melt PSAs, which include styrene block copolymers (SBC), show the greatest flexibility in terms of elastic and viscoelastic modulus. Block copolymers have unique characteristics: their physical properties produce very high adhesive and shear resistance values, which actually exceed those of natural rubber.

Styrene block copolymers are the most common category of thermoplastic elastomers, and combine the mechanical properties of rubber with the processability characteristics of thermoplastics. These copolymers consist of at least three blocks: two endblocks, formed by polystyrene, which gives them characteristics of rigidity, and the midblock, which gives flexibility to the polymer.

When the midblock consists of butadiene, the polymer acquires the ideal feature for use as a pressure-sensitive adhesive. Butadiene possesses an elastic modulus greater than isoprene, and is more difficult to render adhesive; it is therefore far more complex to obtain the right balance between adhesive properties (tack, peel, and creep resistance) and those influenced by temperature. If the temperature is increased above the glass transition temperature (Tg) of polystyrene (±100° C.), its domains disintegrate, and the SBC copolymer becomes indictable as thermoplasts. When solidified, SBC exhibit good elastomeric properties, and tensile strength is higher than for unreinforced vulcanised rubber.

This category of copolymers is mainly used to promote the performance of bitumens in road paving and as a coating material, guaranteeing excellent performance even under extreme weather conditions. They are widely used in the automobile industry, for the manufacture of toys and personal hygiene products, and as packaging material. In recent years they have also been studied in the pharmaceutical field, not only as adhesive copolymers in protective patches but above all as PSAs in systems designed for topical use.

The preparation of patches with a polymer matrix consisting of SBC involves a manufacturing process wherein the copolymer is heated to temperatures exceeding 150° C. in order to melt and make it processable. During the manufacturing process, the excipients are added under stirring, and the mixture can reach temperature peaks close to 200° C. When a homogenous mixture has been obtained, it can be processed by extrusion, rolling, spraying or casting. In the latter case, however, the mixture is left to cool, and a blend is obtained; the blend is then solubilised using a limited range of highly toxic solvents such as toluene, tetrahydrofuran and cyclohexane.

The need to process these copolymers at high temperatures is a drawback in terms of process costs and stability of the active ingredients, which are subjected to thermal stress for long time.

WO 99/53357 discloses the possible use of polymers belonging to different chemical classes to form transparent films designed to be affixed to slides for microbiological tests. It therefore does not describe a preparation for human use, and gives a single example in which toluene (well known for its compatibility with these polymers) is used as solvent.

U.S. Pat. No. 4,728,572 discloses the preparation of PSA by the hot-melt process. As indicated in the examples: "all adhesive formulations were prepared in a Sigma mixer heated to 170° C. by blending the components until homogeneous", and a SEBS copolymer, made with a hot-melt preparation process, is also described.

U.S. Pat. No. 5,527,536 also discloses the patented hot-melt technology, and confirms the well known solubility of SEBS in toluene and petroleum benzine.

EP 885942 discloses formulations obtained by the hot-melt process.

DESCRIPTION OF THE INVENTION

It has now been found that an adhesive system for patches can be formulated which eliminates the drawbacks of the prior art by using a styrene-ethylene/butylene-styrene (SEBS) copolymer solubilised in a mixture of ethyl acetate and oil.

A first aspect of the present invention therefore relates to transdermal or topical formulations in the form of patches characterised by the use of a PSA consisting of a styrene-ethylene/butylene-styrene (SEBS) copolymer with an oil/ethyl acetate base, a hydrogenated resin, and a pharmaceutical or cosmetic active ingredient.

Styrene block copolymers are known for their insolubility in most solvents.

In view of the presence of both aliphatic and aromatic segments, it is known that these elastomers can only be solubilised with aromatic and hydrocarbon solvent systems, or with an aromatic/aliphatic solvent mixture.

It has now surprisingly been discovered that SEBS copolymers can be solubilised with a solvent in which they are notoriously insoluble, namely ethyl acetate, due to the presence of an oil as diluent. A particular affinity has in fact been found between the copolymer and some specific oils which achieve a critical balance between the constituents of the mixture. This binary system allows the solvent to be incorporated without giving rise to opacification (evidence of insolubility), and allows the copolymer to be maintained in solution without swelling.

The present invention shows numerous advantages, including the possibility of conducting the process at room temperature, especially in the case of the SEBS with the lowest molecular weights, thus allowing the incorporation of thermolabile active ingredients which cannot be used in a hot-melt process. Moreover, ethyl acetate is a class 3 solvent (ICH TOPIC Q3C (R3)), and consequently safer for humans, easily removable during the drying process, and with a lower environmental impact than solvents known from the prior art. All this also involves lower manufacturing costs.

The patches obtainable with the adhesive system according to the invention show excellent adhesive and cohesive properties which allow long lasting applications, and withstand the tangential stresses due to movements of the skin. Their excellent adhesive properties are important to ensure better release of the active ingredient; the matrix obtained is occlusive, and passively performs a promoting effect. The formulation is also versatile, because its adhesive and cohesive properties can be modulated as required.

Any SEBS copolymer, with high molecular weight (approx. 198 g/mol $10^3$) or low molecular weight (approx. 58 g/mol $10^3$), can be used according to the invention. SEBS copolymers are available on the market from several suppliers, such as Polimeri Europa (San Donato Milanese, Milan, Italy), under the trade name of Sol TH®.

The preferred polymer concentrations are between 3% and 30%, preferably between 12 and 20%.

The oils that allow the copolymer to be dissolved and maintained in solution are present in concentrations from 10 to 40%, and are preferably chosen from paraffin oils, long-chain hydrocarbon oils such as isopropyl myristate and isopropyl palmitate, bis (2-ethylhexyl) adipate, and oils of natural origin such as almond oil. Paraffin oils, which are normally used as diluents in the preparation of mixtures based on SIS copolymers, have also proved to be useful in the case of SEBS copolymers. Suitable paraffin oils are available on the market under the brands Kaydol®, marketed by Crompton-Witco, Hyprene P100N® (Ergon-West Virginia), Paralux 60® (Chevron-West Virginia), and Lubepharm white FDA 15-17-32-46-68®.

The ethyl acetate concentration is between 10 and 40%. Said concentration depends on the type of oil used: excess solvent can lead to the formation of an opalescent patina due to the precipitation of the polymer.

In order to make the system adhesive, a tackifier must be added at concentrations from 28 to 70%. In view of the purpose of the adhesive system according to the invention, which involves prolonged contact with the skin surface, the aliphatic hydrocarbon resins Regalite R1100® and Piccotac® 1095-N, both marketed by Eastman, or the various Dercolytes® marketed by Les Dérivés Résiniques et Terpéniques, are preferred.

However, other aliphatic, cycloaliphatic, aliphatic/aromatic and cycloaliphatic/aromatic resins can also be used, preferably endblock resins, which act by bonding with the non-elastomer domains of the adhesive.

Both cosmetic and pharmaceutical active ingredients can be incorporated in the matrix thus formulated.

Examples of cosmetic active ingredients include pure, glycolic and water-alcohol extracts of substances of plant origin such as soya, escin, bromelain, caffeine, green tea, *Fucus vesciculosus, Boswellia serrata, Aloe vera*, vitamins such as vitamin E, bleaching substances such as cogic acid, arbutin, azelaic acid, acne treatments such as acetylsalicylic acid and tropolone, and stretch mark treatments such as panthenol and essential oils.

Pharmaceutical active ingredients which can be advantageously formulated in transdermal or topical forms using the adhesive according to the invention are all those suitable for said administration route which present the necessary characteristics of permeation through the skin. Examples of pharmaceutical active ingredients according to the invention therefore include non-steroidal anti-inflammatory drugs (diclofenac, ketoprofen, ibuprofen, naproxen and salts thereof) or steroidal anti-inflammatory drugs (cortisone), muscle relaxants (thiocolchicoside), narcotic analgesics (fentanyl), local anaesthetics (lidocaine, mephenesin), vasoactive substances (nitroglycerin, isosorbide dinitrate); cardiotonics (digoxin); $Ca^{++}$ channel blockers (nifedipine and other dihydropyridines); antiarrhythmia drugs (propranolol and other beta-blockers); motion sickness drugs (dimenhydrinate); antiemetics (ondansetron); anti-Parkinson's drugs (lisuride); bronchodilators (theophylline, salbutamol and other beta-agonists); substances used to treat smoking addiction (nicotine); antibacterials/antibiotics (rifampicin), antifungals (miconazole and other azoles), antihypertensives (clonidine), antivirals (acyclovir), psychoactive drugs (barbital), and tranquillisers (diazepam and other benzodiazepines).

Absorption promoters and antioxidants such as oleic acid, Surfadone®, LP 100, LP300, propylene glycol, terpenes, Transcutol®, Azone®, sodium hydrosulphite, butylhydroxytoluene and BHA can be added to the formulation.

If the active ingredients tend to crystallise, a crystallisation inhibitor such as polyvinylpyrrolidone, acrylic and methacrylic acids, surfactants and other macromolecules can be added to the system.

A preservative such as methyl para-hydroxybenzoate, propyl para-hydroxybenzoate, chlorocresol, chlorphenesin, methylpropanediol, potassium sorbate or benzyl alcohol can be added.

It may be necessary to add a co-solvent such as triacetin, tributyl citrate, propylene glycol, glycerol, benzoate esters, saturated and unsaturated fatty acids.

If the addition of one or more excipients alters the viscosity of the mixture, a rheological modifier such as PVP can be added.

If the formulation contains photosensitive substances, physical filters such as silica and titanium dioxide, or chemical filters such as cinnamates, benzophenones, para-aminobenzoic acid esters and dibenzoylmethanes can be added.

The invention is described in greater detail in the Examples below.

EXAMPLES 1-5

TABLE

| | FORMULATIONS | | | | |
|---|---|---|---|---|---|
| Composition | Example 1 | Example 2 | Example 3 | Example 4 | Example 5 |
| Sol TH 2311 | 12 | 12 | 13.2 | | |
| Sol TH 2312 | | | | 10 | 9 |
| Piccotac 1095-N | 29 | | | | |
| Regalite R1100 | | 28 | 31.5 | | |
| Dercolyte TS 105 | | | | 30 | 51 |
| Liquid paraffin | 30 | | | 25 | |
| Isopropyl myristate | | | 13.2 | 5 | 10 |
| Almond oil | | 12 | | | |
| Ethyl acetate | 29 | 48 | 42.1 | 30 | 30 |

All the formulations described above were prepared using a mixer with a blade stirrer.

It is advisable to leave the copolymer and oil in contact for several hours before preparing the mixture, especially in the case of copolymers with higher molecular weights.

If the mixture is slightly heated at a temperature close to 50° C., the preparation time will be significantly reduced, especially when copolymers with a high molecular weight are used.

When a copolymer with a high molecular weight is used, it may be necessary to increase the resin content, because it is more difficult to obtain a system with good adhesive properties. In fact, the large amount of oil required to "wet" the copolymer drastically reduces the adhesion properties, which can be compensated by increasing the concentration of tackifier resin.

The mixtures were spread on a suitable liner to a thickness of 300 μm, dried at 80° C. for 15 minutes and covered with the chosen protective foil (backing). Either breathable materials (fabric or non-woven fabric, polyurethane) or non-breathable materials (such as polyethylene, and polyolefin foams) can be used as backing.

All patches present good adhesive and cohesive properties, and can be removed easily without causing pain, and without leaving residues on the skin. As regards example 5, the patch prepared is highly adhesive, and is consequently suitable to be applied for long periods. The system still allows painless removal because the polymer is gradually moistened by transepidermal water loss during the application time, which leads to a gradual reduction in adhesion.

Numerous variations can be made to the formulations according to the invention, depending on the aim to be achieved: the concentration of tackifier can be modulated to obtain greater or lesser adhesion, and shear resistance can be modified by changing the oil concentrations. Mixtures of copolymers with different molecular weights can also be prepared to obtain a matrix with different chemico-physical characteristics.

What is claimed is:

1. A self-adhesive matrix system comprising a styrene-ethylene/butylene-styrene copolymer (SEBS) in an oil/ethyl acetate mixture, a hydrogenated resin and a pharmaceutical or cosmetic active ingredient.

2. The system as claimed in claim 1, wherein the oil is selected from the group consisting of paraffin oil, isopropyl myristate, isopropyl palmitate, almond oil and bis (2-ethylhexyl) adipate.

3. The system as claimed in claim 1, wherein the hydrogenated resin is an endblock aliphatic resin.

4. The system as claimed in claim 1, wherein the polymer is present in a concentration ranging from 3% to 30% of the system.

5. The system as claimed in claim 1, wherein the oil is present in a concentration ranging from 10 to 40% of the system.

6. The system as claimed in claim 1, wherein ethyl acetate is present in a concentration ranging from 10 to 40% of the system.

7. The system as claimed in claim 1, wherein the resin is present in a concentration ranging from 28 to 70% of the system.

8. The system as claimed in claim 1, further containing one or more components selected from the group consisting of absorption promoters, antioxidants, co-solvents, crystallization inhibitors, opacifiers, sunscreens, rheology modifiers and preservatives.

9. A patch comprising a liner and the system according to claim 1, wherein the system is spread on said liner.

10. The system as claimed in claim 4, wherein the polymer is present in a concentration ranging from 12 to 20% of the system.

* * * * *